United States Patent
Hong et al.

(10) Patent No.: US 12,129,228 B2
(45) Date of Patent: Oct. 29, 2024

(54) CONTINUOUS SYNTHESIS METHOD FOR 1,1'-BICYCLIC [1.1.1]PENTANE-1,3-DIETHYL KETONE COMPOUNDS

(71) Applicant: JILIN ASYMCHEM LABORATORIES CO., LTD., Jilin (CN)

(72) Inventors: Hao Hong, Morrisville, NC (US); Enxuan Zhang, Tianjin (CN); Jiangping Lu, Tianjin (CN); Fuliang Wei, Tianjin (CN); Sihang Yang, Tianjin (CN); Guanda Che, Tianjin (CN)

(73) Assignee: JILIN ASYMCHEM LABORATORIES CO., LTD., Jilin (CN)

( * ) Notice: Subject to any disclaimer, the term of this patent is extended or adjusted under 35 U.S.C. 154(b) by 374 days.

(21) Appl. No.: 17/433,826

(22) PCT Filed: Jun. 11, 2019

(86) PCT No.: PCT/CN2019/090736
§ 371 (c)(1),
(2) Date: Aug. 25, 2021

(87) PCT Pub. No.: WO2020/248126
PCT Pub. Date: Dec. 17, 2020

(65) Prior Publication Data
US 2022/0144744 A1    May 12, 2022

(51) Int. Cl.
C07C 45/68    (2006.01)
B01J 19/00    (2006.01)
B01J 19/12    (2006.01)

(52) U.S. Cl.
CPC ........... *C07C 45/68* (2013.01); *B01J 19/0066* (2013.01); *B01J 19/121* (2013.01); *B01J 2219/00033* (2013.01); *C07C 2602/38* (2017.05)

(58) Field of Classification Search
CPC ............................................. C07C 45/68–75
See application file for complete search history.

(56) References Cited

U.S. PATENT DOCUMENTS 5,405,550 A    4/1995 Michl

FOREIGN PATENT DOCUMENTS

| CN | 107486115 A | 12/2017 |
|----|-------------|---------|
| CN | 110204431 A | 9/2019 |

(Continued)

OTHER PUBLICATIONS

Machine translation of CN107486115A, Dec. 19, 2017; pp. 1-5 (Year: 2017).*

(Continued)

*Primary Examiner* — Medhanit W Bahta
(74) *Attorney, Agent, or Firm* — Riverside Law LLP

(57) ABSTRACT

Provided is a continuous synthesis method for 1,1'-bicyclic [1.1.1]pentane-1,3-diethyl ketone compounds. The continuous synthesis method comprises: under the irradiation of a light source, continuously conveying raw material A and raw material B to a continuous reaction device for a continuous photochemical reaction to obtain 1,1'-bicyclic[1.1.1]pentane-1,3-diethyl ketone compounds, and controlling the reaction temperature in the continuous reaction device by a temperature control device during the continuous photochemical reaction. A propellane with substituents, as a reaction raw material, is subjected to the above photochemical reaction in the continuous reaction device to reduce the probability of its slow decomposition and deterioration (Continued)

under the irradiation, and greatly improve the conversion rate of the reaction material and product yield.

17 Claims, 1 Drawing Sheet

(56) References Cited

FOREIGN PATENT DOCUMENTS

| EA | 200600485 A1 | 2/2007 |
|---|---|---|
| JP | 2019510012 A | 4/2019 |
| WO | 2017157932 A1 | 9/2017 |
| WO | 2019051038 A1 | 3/2019 |

OTHER PUBLICATIONS

Britton, J. et al. "The assembly and use of continuous flow systems for chemical synthesis" Nature Protocols, 2017, 2, 2423-2446 (Year: 2017).*

International Search Report (ISR) for PCT/CN2019/090736 mailed Feb. 26, 2020.

Kaszynski, Piotr, and Josef Michl. "A practical photochemical synthesis of bicyclo [1.1. 1] pentane-1, 3-dicarboxylic acid." The Journal of Organic Chemistry 53.19 (1988): 4593-4594 (cited in ISR for PCT/CN2019/090736 mailed Feb. 26, 2020).

Bothe, H., et al., "High Molecular Weight Poly([1.1.1]propellane)s and a New Polyamide with Bicyclo[1.1.1]pentane Fragments," Advanced Materials, vol. 3, No. 9 (1991), pp. 440-442.

Elliott, L. D., et al., "Batch versus Flow 1-10 Photochemistry: A Revealing Comparison of Yield and Productivity," Chemistry—A European Journal, vol. 20 (2014), pp. 15226-15232.

European Office Action for EP 19933011.9, mailed Apr. 26, 2024, 8 Pages.

European Search Report for EP 19933011, mailed Aug. 2, 2022, 12 Pages.

Levin, M. D., et al., "Preparation, Strucure, and Properties of Symmetrically 1,2-Difunctionalized Penta- and Hexafluorobicyclo[1.1.1]pentanes," Journal of the American Chemical Society, vol. 119, No. 52 (1997), pp. 12750-12761.

* cited by examiner

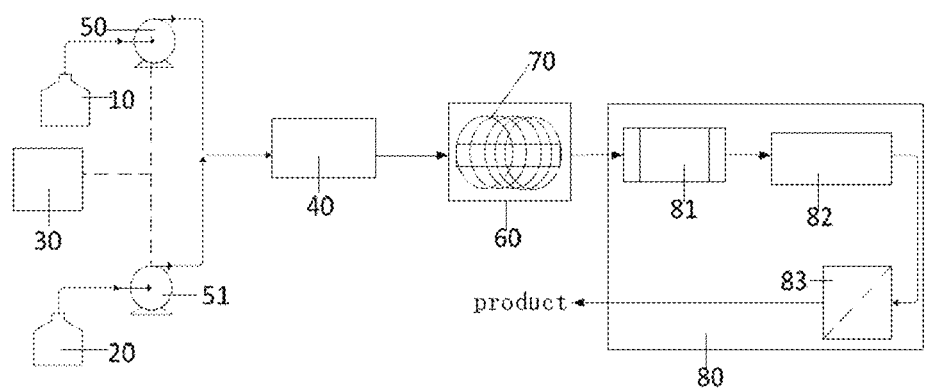

CONTINUOUS SYNTHESIS METHOD FOR 1,1'-BICYCLIC [1.1.1]PENTANE-1,3-DIETHYL KETONE COMPOUNDS

CROSS-REFERENCE TO RELATED APPLICATIONS

This application is the U.S. national phase application filed under 35 U.S.C. § 371 claiming benefit to International Patent Application No. PCT/CN2019/090736, filed on Jun. 11, 2019, the disclosure of which is incorporated herein by reference in its entirety.

TECHNICAL FIELD

The present disclosure relates to the field of drug intermediate synthesis, and specifically, relates to a continuous synthesis method for compounds of formula (III).

BACKGROUND

As a non-natural amino acid, 1-aminobicyclic [1.1.1]pentane-1-formic acid has great potential in the field of pharmaceutical chemical research, and is very expensive. 1,1'-bicyclic[1.1.1]pentane-1,3-diethyl ketone is an important intermediate to synthesize 1-aminobicyclic [1.1.1]pentane-1-formic acid, and also a building block to synthesize various kinds of symmetric propellane derivatives, and may be further functionalized to obtain a series of acids, esters, alcohols, amides and other propellane derivatives. Due to the particularity of a substrate, there is a few of report on the synthesis of 1,1'-bicyclic[1.1.1]pentane-1,3-diethyl ketone.

The existing synthetic methods are batch synthesis methods. Propellane and 2,3-butanedione, as substrates, are subjected to light irradiation for a long time to perform free radical addition reaction to be prepared into 1,1'-bicyclic [1.1.1]pentane-1,3-diethyl ketone. For example, the existing literature has reported that 1,1-dibromo-2,2-dichloromethyl cyclopropane, as a starting material, is firstly reacted with methyl lithium, and then subjected to steamed stuff; and the stuff is illuminated with 2,3-butanedione under ice-water bath conditions to obtain a target product. And the total yield of two steps is 58%. But the reaction requires a long irradiation time and has a slow reaction conversion, thereby leading to small-scale preparation of 1,1'-bicyclic [1.1.1] pentane-1,3-diethyl ketone in a laboratory only, incapable of achieving enlarged production. There are similar literature reports subsequently, but the problem of low reaction efficiency has been not solved all the time, such that such kind of compound and downstream products thereof are extremely expensive.

Based on this, there are problems of low reaction efficiency and poor yield in the existing synthetic method. Moreover, the instability problem still exists in propellane as a reaction substrate and products. And propellane will be slowly decomposed by itself under the irradiation, thus being incapable of achieving effective transformation. Meanwhile, the product will go bad under the irradiation.

In view of the above problems, it is necessary to provide a novel synthesis method for compounds of formula (III), thus improving the conversion rate and reaction rate.

SUMMARY

The major objective of the present disclosure is to provide a continuous synthesis method for compounds of formula (III), thus solving a problem that in the synthesis process of compounds of formula (III), the instability of reaction materials and products would lead to low conversion rate of the reaction materials and low product yield.

To achieve the above objective, the present disclosure provides a continuous synthesis method for compounds of formula (III):

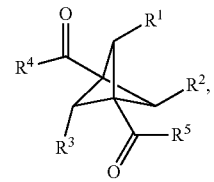

the continuous synthesis method comprises: continuously conveying raw material A and raw material B to a continuous reaction device for a continuous photochemical reaction under irradiation of a light source to obtain the compounds of formula (III), and controlling the reaction temperature in the continuous reaction device by a temperature control device during the continuous photochemical reaction, where the raw material A has a structure represented by formula (I), and the raw material B has a structure represented by formula (II):

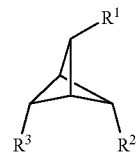

in formula (I), $R^1$, $R^2$, and $R^3$ are each independently selected from hydrogen, benzyl, alkyl, aryl, halogen, ester group, carboxyl or hydroxy and at least one of $R^1$, $R^2$ and $R^3$ is not hydrogen;

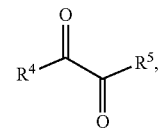

in formula (II), $R^4$ and $R^5$ are each independently selected from hydrogen, alkyl or aryl.

Further, $R^1$, $R^2$ and $R^3$ are each independently selected from hydrogen, benzyl, methyl, phenyl or hydroxy; $R^4$ and $R^5$ are each independently selected from hydrogen, methyl, benzyl or phenyl.

Further, before the continuous photochemical reaction, the continuous synthesis method further comprises: mixing the raw material A with a solvent to form a mixed solution, and then conveying the mixed solution to the continuous reaction device;
preferably, the solvent is one or more selected from a group consisting of n-hexane, n-heptane, n-butyl ethere, cyclohexane and cyclopentane.

Further, the light source is an LED lamp having a wavelength of 300 to 350 nm.

Further, the reaction temperature of the continuous photochemical reaction is 0 to 30° C., preferably 0 to 5° C.

Further, the reaction time of the continuous photochemical reaction is 10 to 20 min.

Further, during the continuous photochemical reaction, the continuous synthesis method further comprises continuously conveying a cosolvent to the continuous reaction device.

Further, the cosovent is one or more selected from a group consisting of methanol, ethanol, ethyl acetate, ethyl formate, acetone, butanone and acetonitrile.

Further, the molar ratio of the raw material A to the raw material B is 1:(1.0 to 1.5).

Further, the continuous reaction device is selected from a continuous reaction coil or a column reactor.

Based on the technical solution of the present disclosure, the free radical formed by propellane with substituents has higher stability; therefore, propellane with substituents serves as the reaction material to greatly improve the stability of the reaction material, reduce the probability of slow decomposition and degeneration under the irradiation, thus improving the conversion rate of the reaction material and yield of the target product (compounds of formula (III)) to some extent. Meanwhile, in the above photochemical reaction process, reaction materials are continuously conveyed to the continuous reaction device, which saves reaction time and achieves high product yield. The present disclosure can reduce the probability that the reaction material and product are destroyed, and greatly improves the conversion rate of the reaction material and product yield. Furthermore, the above continuous synthesis method also effectively solves the problem existing in the enlarged process of the reaction (such as, feasibility and efficiency), which provides a possibility for the industrial production of compounds of formula (III).

BRIEF DESCRIPTION OF THE DRAWINGS

Drawings of the description constituting a portion of the present disclosure are used to further understand the present disclosure; and schematic examples and specification thereof of the present disclosure are used to explain the present disclosure, and are not intended to limit the present disclosure improperly. In the drawings:

The Figure is a structure diagram showing a preferred continuous synthesis device of compounds of formula (III) in the present disclosure.

The above drawings include the following denotation:
10: first feeding device; 20: second feeding device; 30: automatic feed system; 40: mixer; 50: first piston pump; 51: second piston pump; 60: continuous photochemical reaction device; 70: light source; 80: post-processing device; 81: film evaporator; 82: continuous crystalizer; 83: filter.

DETAILED DESCRIPTION OF THE EMBODIMENTS

It should be noted that the examples of the present application and the characteristics of the examples can be mutually combined under the condition of no conflict. The present disclosure will be described specifically in combination with examples hereafter.

As described in the background art, there exists the problem that in the synthesis process of compounds of formula (III), the instability of reaction materials and products would lead to low conversion rate of the reaction materials and low product yield. To solve the above technical problems, the present disclosure provides a continuous synthesis method for compounds of formula (III):

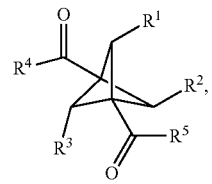

where the continuous synthesis method comprises: continuously conveying raw material A and raw material B to a continuous reaction device for a continuous photochemical reaction under irradiation of a light source to obtain the compounds of formula (III), and controlling the reaction temperature in the continuous reaction device by a temperature control device during the continuous photochemical reaction, where the raw material A has a structure represented by formula (I), and the raw material B has a structure represented by formula (II):

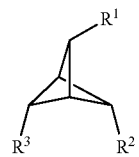

in formula (I), $R^1$, $R^2$ and $R^3$ are each independently selected from hydrogen, benzyl, alkyl, aryl, halogen, ester group, carboxyl or hydroxy; and at least one of $R^1$, $R^2$ and $R^3$ is not hydrogen;

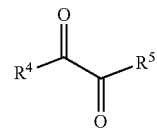

in formula (II), $R^4$ and $R^5$ are each independently selected from hydrogen, alkyl or aryl.

The free radical formed by propellane with substituents has higher stability; therefore, propellane with substituents serves as the reaction material to greatly improve the stability of the reaction material, reduce the probability of slow decomposition and degeneration under the irradiation, thus improving the conversion rate of the reaction material and yield of the target product (compounds of formula (III)) to some extent. Meanwhile, in the above photochemical reaction process, reaction materials are continuously conveyed to the continuous reaction device, which saves reaction time and achieves high product yield. The present disclosure can reduce the probability that the reaction material and product are destroyed, and greatly improves the conversion rate of the reaction material and product yield. Furthermore, the above continuous synthesis method also effectively solves the problem existing in the enlarged process of the reaction (such as, feasibility and efficiency), which provides a possibility for the industrial production of compounds of formula (III).

To further improve the conversion rate of the continuous photochemical reaction, preferably, $R^1$, $R^2$ and $R^3$ are each independently selected from hydrogen, benzyl, methyl, phenyl or hydroxy; $R^4$ and $R^5$ are each independently selected from hydrogen, methyl, benzyl or phenyl. In a preferred embodiment, before the continuous photochemical reaction, the continuous synthesis method further comprises: mixing the raw material A with a solvent to form a mixed solution, and then conveying the mixed solution to the continuous reaction device. Raw material A and the solvent are mixed to form a mixed solution, then the mixed solution is conveyed to a continuous reaction device, which is beneficial to further improving the stability of the reaction materials, thereby facilitating the improvement in the conversion rate of the reaction material and the yield of target products. More preferably, the solvent includes one or more selected from a group consisting of n-hexane, n-heptane, n-butyl ethere, cyclohexane and cyclopentane. Compared with other solvents, the above several solvents and raw material A have better compatibility, thus being beneficial to further improving the stability of the raw material A.

The existing photochemical reaction process usually uses a high-pressure mercury lamp for strong light exposure, and the equipment will give off lots of heat after running for a long time, which causes a great potential risk in tank reaction. To solve the above technical problem, in a preferred example, the light source is an LED lamp with a wavelength of 300 to 350 nm. Compared with the traditional high-pressure mercury lamp, the use of the above LED lamp with the wavelength as a light source can reduce the risk of using the equipment and lower the equipment investment.

In a preferred example, the reaction temperature of the continuous photochemical reaction is 0 to 30° C. The reaction temperature of the continuous photochemical reaction includes, but not limited to, the above scope, and the above temperature scope is beneficial to improving the conversion rate of reaction materials and the yield of target products during the reaction process of the continuous photochemical reaction. More preferably, the reaction temperature of the continuous photochemical reaction is 0 to 5° C.

To improve the full extent of reaction of the raw material A and raw material B, thus further improving the yield of the target product, preferably, the reaction time of the continuous photochemical reaction is 10-20 min.

In a preferred example, during the continuous photochemical reaction, the continuous synthesis method further comprises: continuously conveying a cosolvent to the continuous reaction device. The addition of the cosolvent in the continuous photochemical reaction can not only improve the compatibility of the raw material A and raw material B, but also can dissolve the target products compounds of formula (III) generated by the reaction, thus discharging the cosolvent better and reducing the probability of occurrence of the side reaction. Further, the cosovent includes but not limited to one or more selected from a group consisting of methanol, ethanol, ethyl acetate, ethyl formate, acetone, butanone and acetonitrile.

In a preferred example, the molar ratio of the raw material A to the raw material B is 1:(1.0 to 1.5). The molar ratio of the raw material A to the raw material B includes but not limited to the above scope, and the above scope is beneficial to further improving the yield of the target products, compounds of formula (III).

The existing batch reaction process adopts a tank reactor, and demands for a relatively high requirement of the equipment; influenced by the material, the batch reaction cannot be put into mass production. To solve the above problem, in a preferred example, the continuous reaction device is selected from a continuous reaction coil or a column reactor.

To understand the above technical solution better, the present application further provides a preferred continuous synthesis device for synthesizing compounds of formula (III). As shown in the Figure, the continuous synthesis device includes: a first feeding device 10, a second feeding device 20, an automatic feed system 30, a mixer 40, a first piston pump 50, a second piston pump 51, a continuous photochemical reaction device 60 (a reaction coil), a light source 70 and a postprocessing device 80 (a continuous concentrated crystallization unit); and the postprocessing device 80 includes a film evaporator 81, a continuous crystalizer 82 and a filter 83. The first feeding device 10 is provided with a raw material A inlet, a solvent inlet and a mixed solution outlet. The second feeding device 20 is provided with a raw material B inlet and raw material B outlet. The mixer 40 is provided with a feed port and a reaction material outlet, and the above feed port and mixed solution outlet are communicated with each other via a mixed solution conveying pipeline, and the first piston pump 50 is set on the mixed solution conveying pipeline. The above feed port is communicated with the raw material B outlet via a raw material B conveying tube, and the second piston pump 51 is set on the raw material B conveying tube. Meanwhile, the automatic feed system 30 controls the feed rate of the first piston pump 50 and the second piston pump 51. The continuous photochemical reaction 60 is provided with a reaction material inlet and a product outlet; and the reaction material inlet and reaction material outlet are communicated via a reaction material conveying tube; the first piston pump 50 is arranged on the conveying tube, and the product outlet is communicated with an inlet end of the postprocessing device 80; in the postprocessing device 80, the product system is successively processed by the film evaporator 81, continuous crystalizer 82 and the filter 83 to obtain the required compounds of formula (III); and the light source 70 acts on irradiating the continuous photochemical reaction device.

The present application will be further described specifically in combination with detailed examples, and these examples should not be construed as limiting the protection scope of the present application.

"Equiv." in the present application denotes a multiple of mole number, for example, the amount of 2,3-butanedione required by 1 mol propellane is 1.1 mol, and also denoted as 1.1 equiv.

In the example, the device as shown in the Figure is used to synthesize compounds of formula (III).

Comparative Example 1

1.5 kg n-butyl ether solution of [1.1.1] propellane was homemade, (NMR content was 6.7, equivalent to 100 g raw material) and added to a first feeding device. 143 g (1.1 equiv.) 2,3-butanedione and 200 ml cosolvent (ethanol) were added to a second feeding device, then mixed into a homogeneous solution. A light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 2 g/min, and then to the continuous reaction device (coil) for reaction; outdoor bath had a temperature controlled within 0-5° C. and retention time of 15 min; a discharge port was connected with a film concentration device for continuous concentration; the a concentrated solution entered to an oscillator, and a temperature was controlled within −55° C. to −60° C., on-line crystallization and filteration were performed and white solid was 195.67 g and yield was 85%.

Example 1

1.56 kg n-butyl ether solution of 2-methyl-2-phenyl-tricyclo[1.1.1.0$^{1,3}$] pentane was homemade, (NMR content was 5.0%, equivalent to 78 g raw material) and added to a first feeding device. 143 g (1.1 equiv.) 2,3-butanedione and 200 ml ethanol (cosolvent) were added to a second feeding device, then mixed into a homogeneous solution; a light source (a LED lamp with a wavelength of 313 nm) was turned on and the automatic feed system was opened. By a piston pump, raw material A solution and 2,3-butanedione ethanol solution entered to an on-line mixer respectively at the rate of 10 g/min and 1.93 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 145.8 g and yield was 94%.

Example 2

Example 2 differed from Example 1 in that the temperature of the outdoor bath was 20° C.

1.56 kg n-butyl ether solution of [1.1.1] propellane was homemade, (NMR content was 5.0%, equivalent to 78 g raw material) and added to a first feeding device; 143 g (1.1 equiv.) 2,3-butanedione and 200 ml ethanol (cosolvent) were added to a second feeding device, then mixed into a homogeneous solution; a light source (a LED lamp with a wavelength) was turned on, and the automatic feed system was opened. By a piston pump, raw material A solution and 2,3-butanedione ethanol solution entered to an on-line mixer respectively at the rate of 10 g/min and 1.93 g/min, and then to the continuous reaction device (coil) for reaction; outdoor bath had a temperature controlled within 20° C. and retention time of 15 min; a discharge port was connected with a film concentration device for continuous concentration; a concentrated solution entered to an oscillator, and a temperature was controlled within −55° C. to −60° C., on-line crystallization and filteration were performed a products, and white solid was 120.98 g and yield was 78%.

Example 3

Example 3 differed from Example 1 in that the molar ratio of raw material A to raw material B was 1:2.0.

1.56 kg n-butyl ether solution of 2-methyl-2-phenyl-tricyclo[1.1.1.0$^{1,3}$] pentane was homemade, (NMR content was 5.0%, equivalent to 78 g raw material) and added to a first feeding device; 260.5 g (2.0 equiv.) 2,3-butanedione and 200 ml ethanol (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 4.18 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 108.57 g and yield was 70%.

Example 4

Example 4 differed from Example 1 in that the continuous reaction device was a column reactor. 1.56 kg n-butyl ether solution of 2-methyl-2-phenyl-tricyclo[1.1.1.0$^{1,3}$] pentane was homemade, (NMR content was 5.0%, equivalent to 78 g raw material) and added to a first feeding device; 143 g (1.1 equiv.), 3-butanedione and 200 ml ethanol (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 1.93 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to 60° C., on-line crystallization and filteration were performed. The product (white solid) was 122.52 g and yield was 79%.

Example 5

Example 5 differed from Example 1 in that in raw material A, $R^1$, $R^2$, and $R^3$ were respectively hydrogen, hydrogen and benzyl.

1.5 kg n-butyl ether solution of 2-methyl-2-phenyl-tricyclo[1.1.1.0$^{1,3}$] pentane was homemade, (NMR content was 6.7%, equivalent to 100 g raw material) and added to a first feeding device; 60.6 g (1.1 equiv.), 3-butanedione and 200 ml ethanol (cosolvent) were added to a second feeding device, then mixed into a homogeneous solution; a light source (a LED lamp with a wavelength of 313 nm) was turned on, the automatic feed system was opened. By a piston pump, raw material A solution and 2,3-butanedione ethanol solution entered to an on-line mixer respectively at the rate of 10 g/min and 1.46 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 146.6 g and yield was 94.5%.

Example 6

Example 6 differed from Example 1 in that in raw material A, $R^1$, $R^2$, and $R^3$ were respectively hydrogen, hydrogen and p-methoxybenzyl.

1.5 kg n-butyl ether solution of 2-methyl-2-phenyl-tricyclo[1.1.1.0$^{1,3}$] pentane was homemade, (NMR content was 6.7%, equivalent to 100 g raw material) and added to a first feeding device; 50.8 g (1.1 equiv.), 3-butanedione and 200 ml ethanol (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 1.39 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 138.6 g and yield was 94.8%.

Example 7

Example 7 differed from Example 1 in that in raw material A, $R^1$, $R^2$, and $R^3$ were respectively hydrogen, hydrogen and p-methoxyphenyl.

1.5 kg n-butyl ether solution of 2-p-methoxyphenyl tricyclic[1.1.1.0$^{1,3}$]pentane was homemade, (NMR content was 6.7%, equivalent to 100 g raw material) and added to a first feeding device; 55.0 g (1.1 equiv.) 2,3-butanedione and 200 ml ethanol (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 1.42 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 141 g and yield was 94%.

Example 8

Example 8 differed from Example 1 in that the solved used was n-hexane.

1.5 kg n-butyl ether solution of 2-methyl-2-phenyl-tricyclo[1.1.1.0$^{1,3}$] pentane was homemade, (NMR content was 6.7%, equivalent to 78 g raw material) and added to a first feeding device; 143 g (1.1 equiv.) 2,3-butanedione and 200 ml ethanol (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 1.93 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 141.14 g and yield was 91%.

Example 9

Example 9 differed from Example 1 in that the light source had a wavelength of 365 nm. 1.56 kg n-butyl ether solution of 2-methyl-2-phenyl-tricyclo[1.1.1.0$^{1,3}$] pentane was homemade, (NMR content was 5.0%, equivalent to 78 g raw material) and added to a first feeding device; 143 g (1.1 equiv.), 3-butanedione and 200 ml ethanol (cosolvent) were added to a second feeding device, then mixed into a homogeneous solution; a light source (a LED lamp with a wavelength of 365 nm) was turned on, and the automatic feed system was opened. By a piston pump, raw material A solution and 2,3-butanedione ethanol solution entered to an on-line mixer respectively at the rate of 10 g/min and 1.93 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 131.85 g and yield was 85%.

Example 10

Example 10 differed from Example 1 in that the retention time was 30 min.

1.56 kg n-butyl ether solution of 2-methyl-2-phenyl-tricyclo[1.1.1.0$^{1,3}$] pentane was homemade, (NMR content was 5.0%, equivalent to 78 g raw material) and added to a first feeding device; 143 g (1.1 equiv.), 3-butanedione and 200 ml ethanol (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 5.0 g/min and 1 g/min, and then to the continuous reaction device (coil) for reaction; outdoor bath had a temperature controlled within 0-5° C. and retention time of 30 min; a discharge port was connected with a film concentration device for continuous concentration; a concentrated solution entered to an oscillator, and a temperature was controlled within −55° C. to −60° C., on-line crystallization and filteration were performed. The product (white solid) was 136.48 g and yield was 94%.

Example 11

Example 11 differed from Example 1 in that the cosolvent added was acetonitrile.

1.56 kg n-butyl ether solution of 2-methyl-2-phenyl-tricyclo[1.1.1.0$^{1,3}$] pentane was homemade, (NMR content was 5.0%, equivalent to 78 g raw material) and added to a first feeding device; 143 g (1.1 equiv.) 2,3-butanedione and 200 ml acetonitrile (cosolvent) were added to a second feeding device, then mixed into a homogeneous solution; a light source (a LED lamp with a wavelength of 313 nm) was turned on, and the automatic feed system was opened. By a piston pump, raw material A solution and 2,3-butanedione ethanol solution entered to an on-line mixer respectively at the rate of 10 g/min and 2 g/min, and then to the continuous reaction device (coil) for reaction; outdoor bath had a temperature controlled within 0-5° C. and retention time of 15 min; a discharge port was connected with a film concentration device for continuous concentration; a concentrated solution entered to an oscillator, and a temperature was controlled within −55° C. to −60° C., on-line crystallization and filteration were performed. The product (white solid) was 131.83 g and yield was 85%.

It can be seen from the above description that the examples of the present disclosure achieve the following technical effect:

compared with the existing preparation method, the above propellane with substituents serves as a reaction material to greatly improve the stability of the reaction material, reduce the probability of slow decomposition and degeneration under the irradiation, thus improving the conversion rate of the reaction material and yield of the target product (compounds of formula (III)) to some extent.

The above mentioned are merely preferred examples of the present disclosure, and are not construed as limiting the present disclosure. A person skilled in the art knows that the present disclosure may have various changes and alterations. Any amendment, equivalent replacement, improvement and the like made within the spirit and principle of the present disclosure should be included within the protection scope of the present disclosure.

What is claimed is:

1. A continuous synthesis method for compounds of formula (III):

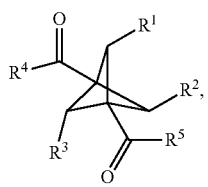

wherein the continuous synthesis method comprises:
continuously conveying raw material A and raw material B to a continuous reaction device for a continuous photochemical reaction under irradiation of a light source to obtain the compounds, and controlling the reaction temperature in the continuous reaction device by a temperature control device during the continuous photochemical reaction, wherein the light source is an LED lamp with a wavelength of 300 to 350 nm, the raw material A has a structure represented by formula (I), and the raw material B has a structure represented by formula (II):

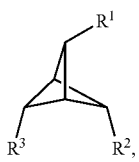

in formula (I) and formula (III), $R^1$, $R^2$, and $R^3$ are each independently selected from hydrogen, benzyl, alkyl, aryl, halogen, ester group, carboxyl or hydroxy, and at least one of $R^1$, $R^2$ and $R^3$ is not hydrogen;

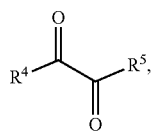

in formula (II) and formula (III), $R^4$ and $R^5$ are each independently selected from hydrogen, alkyl or aryl;
during the continuous photochemical reaction, the continuous synthesis method further comprises continuously conveying a cosolvent to the continuous reaction device, the cosolvent is one or more selected from a group consisting of methanol, ethanol, ethyl acetate, ethyl formate, acetone, butanone and acetonitrile.

2. The continuous synthesis method according to claim 1, wherein $R^1$, $R^2$ and $R^3$ are each independently selected from hydrogen, benzyl, methyl, phenyl or hydroxy; $R^4$ and $R^5$ are each independently selected from hydrogen, methyl, benzyl or phenyl.

3. The continuous synthesis method according to claim 1, wherein before the continuous photochemical reaction, the continuous synthesis method further comprises: mixing the raw material A with a solvent to form a mixed solution, and then conveying the mixed solution to the continuous reaction device.

4. The continuous synthesis method according to claim 3, wherein the solvent is one or more selected from a group consisting of n-hexane, n-heptane, n-butyl ether, cyclohexane and cyclopentane.

5. The continuous synthesis method according to claim 3, wherein the molar ratio of the raw material A to the raw material B is 1:(1.0 to 1.5).

6. The continuous synthesis method according to claim 1, wherein the reaction temperature of the continuous photochemical reaction is 0 to 30° C.

7. The continuous synthesis method according to claim 6, wherein the reaction temperature of the continuous photochemical reaction is 0 to 5° C.

8. The continuous synthesis method according to claim 1, wherein the reaction time of the continuous photochemical reaction is 10 to 20 min.

9. The continuous synthesis method according to claim 1, wherein the molar ratio of the raw material A to the raw material B is 1:(1.0 to 1.5).

10. The continuous synthesis method according to claim 1, wherein the continuous reaction device is selected from a continuous reaction coil or a column reactor.

11. The continuous synthesis method according to claim 2, wherein before the continuous photochemical reaction, the continuous synthesis method further comprises: mixing the raw material A with a solvent to form a mixed solution, and then conveying the mixed solution to the continuous reaction device.

12. The continuous synthesis method according to claim 11, wherein the solvent is one or more selected from a group consisting of n-hexane, n-heptane, n-butyl ether, cyclohexane and cyclopentane.

13. The continuous synthesis method according to claim 2, wherein the reaction temperature of the continuous photochemical reaction is 0 to 30° C.

14. The continuous synthesis method according to claim 13, wherein the reaction temperature of the continuous photochemical reaction is 0 to 5° C.

15. The continuous synthesis method according to claim 2, wherein the reaction time of the continuous photochemical reaction is 10 to 20 min.

16. The continuous synthesis method according to claim 2, wherein during the continuous photochemical reaction, the continuous synthesis method further comprises continuously conveying a cosolvent to the continuous reaction device.

17. The continuous synthesis method according to claim 2, wherein the molar ratio of the raw material A to the raw material B is 1:(1.0 to 1.5).

\* \* \* \* \*